United States Patent
Greiser et al.

(10) Patent No.: US 11,940,518 B2
(45) Date of Patent: Mar. 26, 2024

(54) METHOD AND APPARATUS FOR IMAGING A JAW REGION

(71) Applicant: Siemens Healthcare GmbH, Erlangen (DE)

(72) Inventors: Andreas Greiser, Erlangen (DE); Carmel Hayes, Munich (DE); Mario Zeller, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 64 days.

(21) Appl. No.: 17/704,874

(22) Filed: Mar. 25, 2022

(65) Prior Publication Data
US 2022/0308144 A1 Sep. 29, 2022

(30) Foreign Application Priority Data
Mar. 29, 2021 (DE) ...................... 10 2021 203 136.6

(51) Int. Cl.
| | | |
|---|---|---|
| *G01V 3/00* | (2006.01) | |
| *A61B 5/00* | (2006.01) | |
| *G01R 33/483* | (2006.01) | |
| *G01R 33/54* | (2006.01) | |

(52) U.S. Cl.
CPC ............ *G01R 33/543* (2013.01); *A61B 5/004* (2013.01); *G01R 33/4838* (2013.01); *A61B 5/4542* (2013.01)

(58) Field of Classification Search
CPC .............. G01R 33/3415; G01R 33/543; G01R 33/5659; G01R 33/36; A61B 5/055
USPC ....................................................... 324/307
See application file for complete search history.

(56) References Cited

U.S. PATENT DOCUMENTS

| | | | |
|---|---|---|---|
| 2011/0228998 A1 | | 9/2011 | Vaidya et al. |
| 2014/0084923 A1 | | 3/2014 | Grodzki et al. |
| 2016/0223630 A1 | * | 8/2016 | Abdeddaim ....... G01R 33/3415 |

FOREIGN PATENT DOCUMENTS

| | | | |
|---|---|---|---|
| CN | 1188948 A | * | 7/1998 |
| CN | 107613896 A | * | 1/2018 |
| DE | 10311478 A1 | | 9/2004 |
| DE | 102012217483 A1 | | 3/2014 |

(Continued)

OTHER PUBLICATIONS

JP H07225824 A (Emiiru) (Year: 1995).*

*Primary Examiner* — Walter L Lindsay, Jr.
*Assistant Examiner* — Frederick WEnderoth
(74) *Attorney, Agent, or Firm* — Banner & Witcoff Ltd.

(57) ABSTRACT

The disclosure relates to a technique for providing an image of diagnostically relevant area of a jaw region of a patient by means of a magnetic resonance apparatus by capturing information about the jaw region of the patient, which comprises at least one reference to a position and/or an extent of the diagnostically relevant area of the jaw region. The technique also includes adjusting a parameter of a magnetic resonance measurement as a function of the captured information about the jaw region of the patient, carrying out the magnetic resonance measurement with the adjusted parameter, capturing image data of the jaw region of the patient, reconstructing an image of the diagnostically relevant area of the jaw region as a function of the captured image data, and providing the image of the diagnostically relevant area of the jaw region of the patient.

20 Claims, 5 Drawing Sheets

(56) References Cited

FOREIGN PATENT DOCUMENTS

WO     WO-2012004937 A1 *   1/2012
WO     WO-2014016808 A1 *   1/2014

* cited by examiner

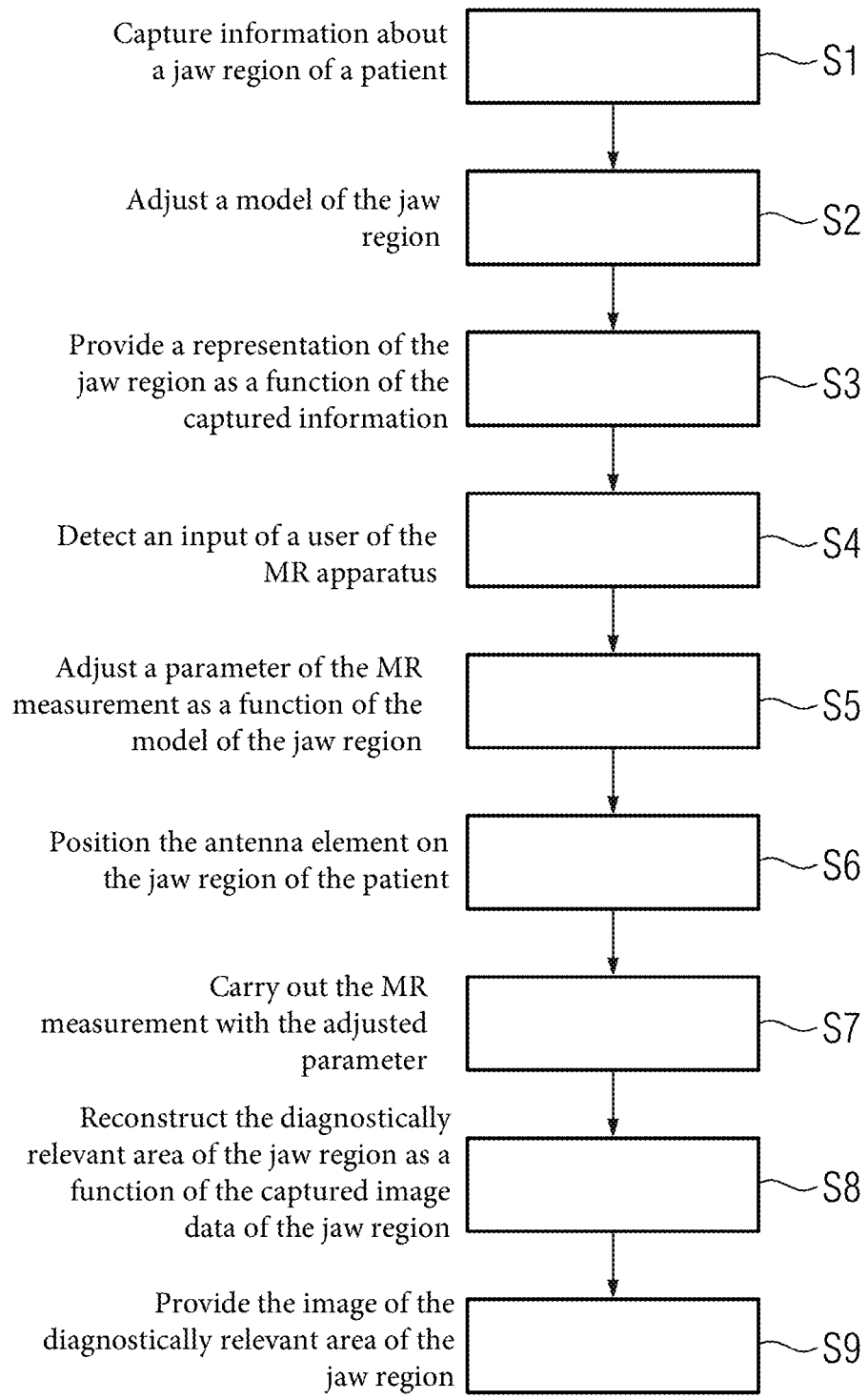

METHOD AND APPARATUS FOR IMAGING A JAW REGION

CROSS-REFERENCE TO RELATED APPLICATIONS

The present application claims the benefit of the filing date of Germany patent application no. DE 10 2021 203 136.6, filed on Mar. 29, 2021, the contents of which are incorporated herein by reference in their entirety.

TECHNICAL FIELD

The disclosure relates to providing an image of a diagnostically relevant area of a jaw region of a patient by means of a magnetic resonance apparatus. The disclosure also relates to a magnetic resonance apparatus comprising a computing unit, wherein the computing unit is designed to coordinate a method and to carry it out by means of the magnetic resonance apparatus.

BACKGROUND

Diseases of the teeth and of the periodontium, such as caries or periodontitis, are usually diagnosed with X-ray based imaging methods. Conventional or digital X-ray projection methods, and recently also three-dimensional X-ray methods, are primarily used in this case. An example of a three-dimensional X-ray method is digital volume tomography, which can be used for imaging teeth and the viscerocranium.

One major drawback of X-ray methods is the need to use ionizing radiation for the imaging. An imaging method, which avoids ionizing rays, is magnetic resonance tomography. This typically enables a better soft tissue contrast than X-ray methods and supports three-dimensional imaging of an examination object as standard. Furthermore, magnetic resonance tomography enables imaging of cysts and detection of degradation of dentin before it can be detected by way of an X-ray method. Magnetic resonance tomography thus represents a potential alternative to known X-ray methods in the imaging of a region of a set of teeth and/or a jaw region as well as the diagnosis of dental diseases of the examination object.

Magnetic resonance tomography is a known imaging method with which magnetic resonance images of the inside of the examination object can be generated. In order to carry out magnetic resonance imaging the examination object is conventionally positioned in a strong, static and homogeneous basic magnetic field (B0 magnetic field) of a magnetic resonance apparatus. The basic magnetic field can have magnetic field strengths of 0.2 tesla to 7 tesla, so nuclear spins of the examination object are oriented along the basic magnetic field. To trigger what are known as nuclear spin resonances, radio-frequency (RF) signals, what are known as excitation pulses (B1 magnetic field), are irradiated into the examination object. Each excitation pulse causes a deviation of a magnetization of particular nuclear spins of the examination object from the basic magnetic field by an amount, which is also known as the flip angle. An excitation pulse can have a magnetic alternating field with a frequency, which corresponds to the Larmor frequency in the case of the respective static magnetic field strength. The excited nuclear spins can have a rotating and decaying magnetization (nuclear spin resonance), which may be detected by means of special antenna as a magnetic resonance signal. Magnetic gradient fields can be overlaid on the basic magnetic field for spatial encoding of the nuclear spin resonances of the examination object.

The received magnetic resonance signals are typically digitized and stored as complex values in a k-space matrix as image data. This k-space matrix can be used as the basis of the reconstruction of magnetic resonance images and for determination of spectroscopy data. The magnetic resonance image is typically reconstructed by means of a multi-dimensional Fourier Transform of the k-space matrix.

SUMMARY

Owing to the avoidance of ionizing radiation, magnetic resonance tomography is particularly suitable for continuous diagnostic monitoring of dental diseases and/or teeth development within the context of a longitudinal imaging study. In longitudinal imaging studies, a plurality of imaging examinations is conventionally carried out to determine a progression of a disease or the success of a therapeutic treatment over a predetermined period.

Previously, magnetic resonance tomography has primarily been carried out in a radiological context accompanied by qualified medical staff, such as radiologists or medical-technical radiology assistants. These qualified staff members are lacking in dental clinical facilities and dental practices, however, so independent preparation and implementation of magnetic resonance measurements and an interpretation of magnetic resonance images represent a great obstacle. Furthermore, the implementation of a magnetic resonance measurement is conventionally associated with a great expenditure of time, which can be a problem for the daily number of patients in such facilities.

It is therefore an object of the disclosure to simplify diagnostic dental imaging by means of magnetic resonance tomography. It is a further object to increase the efficiency of implementation of a magnetic resonance measurement of a jaw region of a patient.

These objects are achieved by the subject matters of the embodiments as discussed herein, including the claims.

A method for providing an image of a diagnostically relevant area of a jaw region of a patient by means of a magnetic resonance apparatus comprises the following steps:

capturing information about the jaw region of the patient, wherein the information about the jaw region comprises at least one reference to a position and/or an extent of the diagnostically relevant area of the jaw region, adjusting a parameter of a magnetic resonance measurement as a function of the captured information about the jaw region of the patient, carrying out the magnetic resonance measurement with the adjusted parameter and capturing image data of the jaw region of the patient, reconstructing an image of the diagnostically relevant area of the jaw region as a function of the captured image data, and providing the image of the diagnostically relevant area of the jaw region of the patient.

A diagnostically relevant area of a jaw region can be, e.g. part of the jaw region, such as a tooth, a section of a tooth, a plurality of teeth, a dental arch, gums, a root of a tooth, a set of teeth, a jawbone, a temporomandibular joint, or the like. It is conceivable that the diagnostically relevant area of the jaw region has a disease and/or an abnormality such as a growth retardation, a growth deformity, a defective position, or the like. Typical examples of diseases of the jaw region are periodontitis, caries, or inflammation of the tooth root. The jaw region of the patient can comprise at least an upper jaw, a lower jaw, and a temporomandibular joint of the patient. In an embodiment, a volume of the jaw region substantially corresponds to a volume which is taken up by the upper jaw, the lower jaw and the temporomandibular joint of the patient.

Information about the jaw region of the patient can be, for example, a diagnostic finding. A diagnostic finding can comprise, e.g., a description of a position and/or an extent of a disease. Furthermore, the information about the jaw region of the patient can comprise image data, such as an X-ray image and/or a magnetic resonance image of a preceding imaging examination of the patient. Capturing such image data can comprise retrieving or receiving information from a medical information system, but also from an internal or external memory unit by means of an interface. It is also conceivable that capturing the information about the jaw region comprises capturing optical image data of the set of teeth of the patient by means of a camera and/or carrying out a localizer measurement for capturing localizer image data by means of the magnetic resonance apparatus. Capturing the information about the jaw region can also comprise applying an image processing algorithm. Such an image processing algorithm can be designed to determine the reference to the position and/or the extent of the diagnostically relevant area of the jaw region as a function of image data and/or an image of the jaw region. The position of the diagnostically relevant area of the jaw region can comprise, e.g., a position of a disease relative to the jaw region of the patient and/or a designation of a tooth and/or a dental arch, which are affected by the disease. Accordingly, the extent of the diagnostically relevant area of the jaw region can describe an area and/or a volume of the jaw region, which is affected by the disease. Apart from a disease the diagnostically relevant area can of course also have further diagnostically relevant aspects, such as a dental developmental disorder, malpositioned teeth, accidental damage or the like.

One parameter of a magnetic resonance measurement can be, inter alia, an imaging parameter, such as an image resolution, a contrast, a slice thickness, a dimension of an imaging volume and the like. It is likewise conceivable that the parameter of the magnetic resonance measurement comprises a group of imaging parameters, an imaging sequence and/or a succession of imaging sequences. Furthermore, the parameter can comprise any setting of the magnetic resonance measurement and/or the progress of the magnetic resonance measurement. It is conceivable that the parameter of the magnetic resonance measurement is adjusted as a function of the captured information about the jaw region of the patient.

Carrying out the magnetic resonance measurement can comprise carrying out one or more imaging sequence(s). This incorporates image data of the jaw region of the patient. Implementation of the magnetic resonance measurement may comprise carrying out an imaging sequence, which is adjusted for imaging teeth. Possible imaging sequences can have, for example, very short echo times in order to compensate a short T2 relaxation time of spins of dentin or tooth enamel and to represent these areas in a signal-intense manner in the image data. Very short echo times can be, for example, less than 150 μs or less than 70 μs. Possible imaging sequences are, for example, FLASH (fast low-angle shot) or UTE (ultra-short echo time) sequences. It is likewise conceivable, however, that imaging sequences with a longer echo time, such as a TSE (turbo spin echo) sequence, are used. With such sequences it is possible to avoid detection of the magnetic resonance signal of the tooth enamel or of the dentin. In image data of such imaging sequences the teeth may be differentiated, for example, by the absence of a signal intensity in contrast to surrounding tissue. In an embodiment, image data is captured by means of an antenna element or a plurality of antenna elements, which are positioned at the jaw region of the patient. The antenna element or the plurality of antenna elements can be configured e.g. to receive magnetic resonance signals of the jaw region and to relay them to a receiving unit of the magnetic resonance apparatus. In an embodiment, the magnetic resonance measurement is carried out with the adjusted parameter in order to capture, e.g., image data of the diagnostically relevant area of the jaw region. This can mean that the imaging volume of the magnetic resonance measurement is restricted or limited as a function of the information about the jaw region.

The image of the diagnostically relevant area of the jaw region can be reconstructed e.g. by means of a computing unit of the magnetic resonance apparatus. In an embodiment, the image is restricted or limited on reconstruction as a function of the information about the jaw region to the diagnostically relevant area of the jaw region. It is conceivable that image data, which lies outside of the diagnostically relevant area of the jaw region, is faded out or separated on reconstruction of the image. It is likewise conceivable that the captured image data is already limited by means of the adjusted parameter of the magnetic resonance measurement accordingly to the diagnostically relevant area of the jaw region of the patient. In this case, the image of the diagnostically relevant area of the jaw region can be reconstructed on the basis of the captured image data of the jaw region of the patient.

Providing the image of the diagnostically relevant area of the jaw region of the patient may comprise generating the image, e.g. at least storing the image on a memory unit of the magnetic resonance apparatus, a medical information system, and/or the cloud. It is also conceivable that the image of the diagnostically relevant area is output by means of an output unit to a user of the magnetic resonance apparatus. An output unit can comprise, for example, a monitor, a touchscreen, a printer or the like. A user can be, for example, a physician, e.g. a dentist, and/or a medical technical assistant or a medical staff member of a dental facility. The user can be positioned at a site of the magnetic resonance apparatus, but also at any other location. For example, the user can be positioned in a different city, a different state, and/or a different country and carry out a remote diagnosis of the image of the diagnostically relevant area of the jaw region of the patient. It is also conceivable that the image of the diagnostically relevant area of the jaw region of the patient is provided to a program or an algorithm (for example "virtual radiologist"), which is designed to categorize an image content, to make a diagnosis and/or propose a treatment. The user and/or the algorithm can also be provided with any information relating to the patient, which is helpful or required for a diagnosis of the image of the diagnostically relevant area of the jaw region of the patient.

By way of the method, image data captured by means of the magnetic resonance measurement may be restricted or limited to a diagnostically relevant area of the jaw region of the patient. Images can be provided thereby, which are individually limited to a volume and/or section of the jaw region of the patient required for a diagnosis. A representation of areas, which conventionally exceed the expertise of dentists can thus advantageously be avoided. As a result, risk of a misdiagnosis of a finding lying outside of the expertise of a dentist can be reduced or prevented. Furthermore, the time taken for carrying out magnetic resonance measurement may advantageously be reduced due to the limitation of the captured image data to the diagnostically relevant area of the jaw region.

In one embodiment of the method, capturing the information about the jaw region of the patient comprises capturing optical image data of the set of teeth of the patient, an X-ray image of the jaw region of the patient, a magnetic resonance image of the jaw region of the patient, and/or localizer image data of the jaw region of the patient.

As described above, the X-ray image and/or the magnetic resonance image of the jaw region of the patient can originate e.g. from a preceding imaging examination and be read or received by means of an interface from a memory unit. It is likewise conceivable, however, that the magnetic resonance image of the jaw region of the patient is captured by means of a magnetic resonance measurement. In an embodiment, a localizer measurement of the jaw region of the patient is carried out for this purpose. The localizer measurement can be taken to mean a time-efficient magnetic resonance measurement in which localizer image data of the jaw region of the patient is captured. The localizer measurement can have restrictions in respect of the quality and/or spatial resolution of the captured localizer image data compared to a conventional magnetic resonance measurement. In an embodiment, the localizer measurement provides a spatial resolution, however, which is suitable for detection and/or identification of anatomical structures, such as a tooth, a dental arch, a jawbone, or the like. The localizer measurement can also comprise a projection measurement. A projection measurement can be a magnetic resonance measurement in which a spatial encoding is omitted in one spatial direction. The localizer image data can thus comprise a two-dimensional projection image of a three-dimensional imaging volume of the jaw region of the patient. It is also conceivable that the localizer image data comprises an image of a localizer measurement, which was acquired during a preceding magnetic resonance measurement.

Optical image data of the set of teeth of the patient may be captured during the capturing of the information about the jaw region by means of a camera, such as a 2D camera, a 3D camera, and/or an infrared camera. It is likewise conceivable, however, that the optical image data, as described above, is retrieved or received from a database or a memory unit.

In one embodiment, capturing the information about the jaw region of the patient comprises at least capturing localizer image data and an X-ray image and/or a magnetic resonance image of the jaw region of the patient, wherein the X-ray image and/or the magnetic resonance image is registered with the localizer image data. In an embodiment, a connection between the diagnostically relevant area of the jaw region and the set of teeth and/or the teeth of the jaw region of the patient can be established. Determination of a position of a disease and/or a relative position or parts or sections of the jaw region of the patient, such as a healthy tooth and a diseased tooth and/or a diseased tooth and a dental arch of a jaw, can thus advantageously be simplified. Furthermore, the localizer image data can be captured during registering with further image data and/or further images with a lower spatial resolution and/or a reduced quality, so the time taken for carrying out the inventive method may advantageously be reduced. Of course, a magnetic resonance image of a preceding and/or a current magnetic resonance measurement can also be registered with optical image data or an X-ray image in order to establish a connection between the diagnostically relevant area of the jaw region and the set of teeth and/or the teeth of the jaw region of the patient.

By capturing one or more of said item(s) of information about the jaw region, the position and/or extent of the diagnostically relevant area of the jaw region may be determined with a higher degree of accuracy. As a result, the imaging volume of the magnetic resonance measurement and/or reconstructing the image may advantageously be restricted with a higher degree of accuracy to the diagnostically relevant area of the jaw region.

In a further embodiment of the method, capturing the information about the jaw region of the patient comprises capturing optical image data of the set of teeth of the patient, wherein adjusting the parameter of the magnetic resonance measurement and/or reconstructing the image of the diagnostically relevant area of the jaw region takes place as a function of the optical image data.

In an embodiment, the optical image data of the set of teeth of the patient is captured, as described above, by means of a camera. It is conceivable that the patient opens their mouth to be able to suitably orient the camera with the set of teeth. It is also conceivable that by means of the camera a plurality of images of the set of teeth is acquired at different opening angles of the upper jaw and of the lower jaw of the patient. As an example, the camera may be a digital camera, which transfers the optical image data of the set of teeth by means of a wired or wireless signal link to the computing unit of the magnetic resonance apparatus and/or a memory unit. It is also conceivable that existing optical image data is read from a database and/or an internal or external memory unit. The computing unit can have an image processing algorithm, which identifies and/or marks anatomical structures, such as teeth, dental arches, jawbones, and the like. It is conceivable that the image processing algorithm determines an absolute position of the diagnostically relevant area and/or a position of the diagnostically relevant area relative to an anatomical structure of the jaw region. The computing unit and/or the image processing algorithm can also be designed to determine the parameter of the magnetic resonance measurement as a function of the absolute position of the diagnostically relevant area and/or the position of the diagnostically relevant area relative to an anatomical structure of the jaw region. The parameter of the magnetic resonance measurement can be determined in such a way that the time taken for carrying out the magnetic resonance measurement is reduced and/or an imaging volume of the magnetic resonance measurement is restricted to the diagnostically relevant area.

In one example, the computing unit determines an imaging parameter of the magnetic resonance measurement in such a way that the imaging volume is substantially limited to the diagnostically relevant area of the jaw region. In a further example, a position of the patient relative to the magnetic resonance apparatus is adjusted by means of a patient positioning apparatus in such a way that the diagnostically relevant area of the jaw region matches an imaging volume of the magnetic resonance apparatus. It is also conceivable that the computing unit determines a position of a local coil and/or an antenna element in such a way that receiving magnetic resonance signals is substantially limited to the diagnostically relevant area of the jaw region.

In one embodiment, capturing optical image data of the set of teeth of the patient comprises capturing a position of at least one marker, which is positioned at the jaw region of the patient, wherein adjusting the parameter of the magnetic resonance measurement takes place as a function of the position of the at least one marker. For instance, the at least one marker may be an optical marker, which has a color, a material, and/or a reflective property, which enables identifying of the at least one optical marker and/or a differentiation of the at least one optical marker from the jaw region of the patient by means of the image processing algorithm on the basis of the optical image data. The at least one marker can comprise, e.g., a magnetic resonance active material such as encapsulated vitamin D, vitamin E, and/or cod liver oil, which during preparation for the magnetic resonance measurement is positioned by the user at the diagnostically relevant area of the jaw region. It is also conceivable that the at least one marker is connected to a dedicated local coil, which is positioned intraorally at the diagnostically relevant area of the jaw region. The at least one marker can be captured and localized e.g. by means of a localizer measurement and/or a magnetic resonance measurement. The position of the at least one marker can be used, as described above, for registering the optical image data of the set of teeth with localizer image data.

By capturing optical image data, a relative position of the diagnostically relevant area and the jaw region of the patient can be captured in a time-efficient manner. As a result, the time taken for the method may be advantageously reduced.

In one embodiment, the method also has the following step:
  adjusting a model of the jaw region of the patient as a function of the captured information about the jaw region of the patient, wherein adjusting the parameter of the magnetic resonance measurement and/or reconstructing the image of the diagnostically relevant area of the jaw region takes place as a function of the model of the jaw region.

A model of the jaw region can comprise an accurate or a simplified representation of the jaw region of the patient. The model of the jaw region can comprise, e.g., information about a structural composition of the jaw region of the patient. For example, the model can have a temporomandibular joint, a jaw, a dental arch, two dental arches, and/or individual teeth, which are substantially positioned in an anatomically correct position relative to each other. The model can also simulate mechanical or biomechanical behavior of the jaw region of the patient and/or be adjusted in accordance with the mechanical behavior of the jaw region of the patient.

As an example, the model of the jaw region may be adjusted as a function of image data and/or an image, such as optical image data, localizer image data, an X-ray image and/or a magnetic resonance image, so an individual shape of the jaw and/or an individual arrangement of teeth of the patient can be reconstructed with the model. The computing unit can carry out registering of image data and/or an image with the model of the jaw region for this purpose. For instance, positions of anatomical structures of the model of the jaw region may be correlated with anatomical structures contained in the image data and/or the image, so the model of the jaw region comprises a representation of the jaw region of the patient. The diagnostically relevant area of the jaw region may also be transferred to the model of the jaw region and/or be registered with it. It is conceivable that adjusting the parameter of the magnetic resonance measurement and/or reconstructing the image of the diagnostically relevant area of the jaw region takes place as a function of the model of the jaw region of the patient.

Apart from the use for a restriction of the magnetic resonance measurement to the diagnostically relevant area of the jaw region, the model of the jaw region of the patient may also be used for a correction of a movement of the patient during the magnetic resonance measurement. For example, a detected movement of the lower jaw of the patient may be reconstructed by means of the model of the jaw region and be considered when reconstructing the image of the diagnostically relevant area. As a result, the quality of the reconstructed image can be increased and/or a repetition of the magnetic resonance measurement can be advantageously avoided.

According to a further embodiment of the method, capturing the information about the jaw region of the patient also comprises ascertaining a relative position of a first anatomical structure of the jaw region of the patient and of a second anatomical structure of the jaw region of the patient, wherein adjusting the parameter of the magnetic resonance measurement takes place as a function of the relative position of the first anatomical structure of the jaw region of the patient and the second anatomical structure of the jaw region of the patient.

As described above, an anatomical structure of the jaw region can comprise a tooth, a dental arch, a jaw or the like. As an example, the relative position of the first anatomical structure of the jaw region of the patient and the second anatomical structure of the jaw region of the patient may be ascertained as a function of optical image data, localizer image data, an X-ray image, and/or a magnetic resonance image. It is conceivable that an image processing algorithm of the computing unit identifies anatomical structures, such as a first tooth and a second tooth of the patient, in the image data and/or an image and ascertains the relative position of the first tooth and of the second tooth. It is also conceivable that the first anatomical structure of the jaw region of the patient and the second anatomical structure of the jaw region of the patient, starting from the image data and/or the image, are firstly registered with the model of the jaw region. The relative position of the first anatomical structure of the jaw region of the patient and of the second anatomical structure of the jaw region of the patient can then be ascertained as a function of the model of the jaw region. The relative position of the first anatomical structure of the jaw region of the patient and the second anatomical structure of the jaw region of the patient can be characterized in particular by a dimension, a coordinate, and/or a plurality of coordinates. The first anatomical structure of the jaw region of the patient and the second anatomical structure of the jaw region of the patient can represent, e.g., parts or sections of the jaw region with a diagnostically relevant area. It is conceivable that the first anatomical structure of the jaw region of the patient and the second anatomical structure of the jaw region of the patient represent separate or unconnected sections of the jaw region of the patient.

As a function of the relative position of a plurality of separate, diagnostically relevant areas of the jaw region of the patient it may be ascertained whether the image data of the diagnostically relevant areas of the jaw region are captured by means of an imaging sequence with a larger imaging volume or by means of a plurality of imaging sequences with smaller, mutually separate imaging volumes. As a result, a time efficiency of the magnetic resonance measurement may advantageously be increased as a function of an individual distribution of diagnostically relevant areas.

In a further embodiment of the method, a plurality of individual slices in the diagnostically relevant area of the jaw region are determined as a function of the information about the jaw region of the patient, wherein adjusting the parameter of the magnetic resonance measurement takes place as a function of the plurality of individual slices, and wherein carrying out the magnetic resonance measurement comprises capturing image data of the plurality of individual slices.

In an embodiment, capturing the information about the jaw region of the patient comprises capturing localizer image data of the jaw region of the patient by means of the magnetic resonance apparatus. It is conceivable that a magnetic resonance-active marker is positioned at the diagnostically relevant area of the jaw region to identify the diagnostically relevant area in the localizer image data. It is also conceivable that the localizer image data is registered with optical image data, a magnetic resonance image, an X-ray image, and/or a model of the jaw region, which contain information about a position of a diagnostically relevant area. For instance, positions of distributed or separate sections of the jaw region with diagnostically relevant areas may be determined as a function of localizer image data. It is conceivable that the diagnostically relevant areas have a small spatial extent but are relatively widely spaced apart from each other. A ratio of spatial extent of a first diagnostically relevant area to a spacing from a second diagnostically relevant area can be, for example, less than 1.5, less than 1, less than 0.5 or less than 0.1. In such cases the jaw region of the patient and/or the diagnostically relevant areas of the jaw region can be divided into a plurality of individual slices for which separate imaging sequences are carried out when capturing the image data. Preferably, imaging parameters, such as an imaging volume, a slice thickness, a resolution or the like are adjusted when adjusting the parameter of the magnetic resonance measurement for each individual slice of the plurality of individual slices, and these are then used when carrying out the magnetic resonance measurement for capturing the image data of the plurality of individual slices.

The plurality of individual slices can be determined in such a way that the diagnostically relevant area of the jaw region, such as a tooth or a plurality of adjacent teeth, are captured by a shared imaging volume of the magnetic resonance measurement. Further anatomical structures of the jaw region of the patient may be excluded from the imaging volume here. A dimension of the imaging volume can thus substantially comprise a dimension of a tooth or a plurality of teeth of the patient. It is likewise conceivable, however, that the plurality of individual slices define two, three, or a plurality of unconnected imaging volumes. When carrying out the magnetic resonance measurement the image data of the plurality of unconnected imaging volumes is preferably captured by means of a plurality of imaging sequences.

In a further embodiment, capturing the information about the jaw region of the patient comprises capturing optical image data of the jaw region of the patient by means of a camera. It is conceivable that an optically active marker is positioned at the diagnostically relevant area of the jaw region to identify the diagnostically relevant area in the localizer image data.

By determining a plurality of individual slices for which image data is captured when carrying out the magnetic resonance measurement, a time efficiency of the magnetic resonance measurement may advantageously be increased compared with a conventional approach in which the imaging volume comprises the entire jaw region of the patient.

In one embodiment of the method, adjusting the parameter of the magnetic resonance measurement comprises at least:
adjusting an imaging parameter of the magnetic resonance measurement,
limiting an imaging volume of the magnetic resonance measurement to the diagnostically relevant area, and/or
adjusting a sampling frequency in a phase-encoding direction.

An imaging parameter of the magnetic resonance measurement can comprise, for example, a resolution, a dimension of an imaging volume, an orientation of the imaging volume, a position of the imaging volume, a slice thickness, a frequency of an excitation pulse, a duration of an excitation pulse and the like. In an embodiment, when adjusting the parameter of the magnetic resonance measurement, at least the imaging volume is matched to the diagnostically relevant area of the jaw region. This can mean that the position and/or the orientation of the imaging volume are set such that the imaging volume is substantially tailored to the diagnostically relevant area. It is conceivable that during adjustment of the imaging volume to the diagnostically relevant area, a portion of anatomical structures, which are located outside of the diagnostically relevant area, is reduced or minimized in the imaging volume. It is also conceivable that imaging parameters are adjusted for a plurality of imaging sequences of the magnetic resonance measurement. An imaging sequence can capture image data of a dedicated individual slice with a diagnostically relevant area. Furthermore, adjusting the parameter of the magnetic resonance measurement can comprise adjusting a phase encoding and/or a frequency encoding. For example, adjusting the parameter of the magnetic resonance measurement can comprise a reduction of a sampling frequency in a phase-encoding direction. Such a reduction in the sampling frequency (Field of View) can promote an occurrence of convolution artifacts, however. It is conceivable that corresponding convolution artifacts are estimated by means of modeling tissue types and their extent in a surrounding volume. In one embodiment, convolution artifacts are avoided as a function of a mechanical or a biomechanical model of the jaw region according to an above-described embodiment.

By adjusting imaging parameters of the magnetic resonance measurement, the imaging volume may be adjusted to the diagnostically relevant area of the jaw region. As a result, the image of the magnetic resonance measurement may be advantageously focused on an area of the jaw region with a disease so the time taken for carrying out the magnetic resonance measurement can be reduced. For instance, the speed of capturing the image data may be increased by means of a reduction in the sampling frequency in the phase-encoding direction. With a declining duration of the magnetic resonance measurement an effect of a movement of the patient on capturing the image data may advantageously also be reduced.

In a further embodiment of the inventive method, carrying out the magnetic resonance measurement comprises at least:
selecting at least one antenna element from a plurality of antenna elements, wherein the image data of the jaw region is captured by means of the at least one selected antenna element,
selective exciting of the diagnostically relevant area of the jaw region by means of an excitation pulse, and/or
saturating nuclear spins in an area outside of the imaging volume by emitting a saturation pulse as a function of the captured information about the jaw region of the patient.

It is conceivable that magnetic resonance signals of the jaw region of the patient are received during the magnetic resonance measurement by means of a dedicated dental coil, which is positioned at the jaw region of the patient. The dental coil can have an antenna element or a plurality of antenna elements, which are positioned locally at the diagnostically relevant area of the jaw region of the patient. In an embodiment, the dental coil has a plurality of antenna elements, which receive magnetic resonance signals from the entire jaw region of the patient. As a function of the ascertained information about the jaw region of the patient at least one antenna element, e.g. two or more antenna elements, can be selected from the plurality of antenna elements, which are positioned at the diagnostically relevant area of the jaw region. The image data of the jaw region of the patient can accordingly be captured by means of the selected antenna element or the plurality of selected antenna elements. It is likewise conceivable, however, that the captured magnetic resonance signals of the plurality of antenna elements are weighted as a function of the captured information about the jaw region. This can mean that magnetic resonance signals are separated from antenna elements whose receiving area is located outside of the diagnostically relevant area of the jaw region of the patient. It is also conceivable that a contribution of such antenna elements to the image of the diagnostically relevant jaw region of the patient is ignored.

In a further example, the antenna elements of the dental coil are also designed for exciting the jaw region. The antenna elements can irradiate a radio-frequency excitation pulse into the jaw region of the patient for this to excite nuclear spins in the jaw region. It is conceivable that a volume of the jaw region excited by an antenna element depends on a position, an orientation, and/or a shape of the antenna element. By means of suitable selection of antenna elements, which are positioned in the vicinity of the diagnostically relevant area of the jaw region, the excitation of tissue in the jaw region can be selectively restricted to the diagnostically relevant area. The antenna elements can be selected, e.g., as a function of excitation profiles of the individual antenna elements and/or groups of antenna elements. Such excitation profiles can be retrieved, for example, from a memory unit of the magnetic resonance apparatus or be ascertained by means of a reference measurement. Selective exciting of the diagnostically relevant area of the jaw region may comprise emitting a multi-dimensional excitation pulse. A multi-dimensional excitation pulse can be characterized e.g. by a complex geometric excitation volume and/or an overlaying of excitation volumes of a plurality of antenna elements.

It is also conceivable that carrying out the magnetic resonance measurement comprises saturating nuclear spins in an area outside of the imaging volume by emitting a saturation pulse. This can mean that, e.g., antenna elements whose excitation volume or excitation profile is located outside of the diagnostically relevant area of the jaw region emit a saturation pulse. Saturation pulses can be repeated e.g. in an interval, which is shorter than a T1 relaxation time of a tissue outside of the imaging volume to be saturated. A tissue to be saturated can be, e.g., tissue of a tongue, a cheek, and/or a palate. A tissue to be saturated can also be soft tissue in the jaw region of the patient.

By selecting antenna elements, but also selective exciting of the tissue of the jaw region, capturing image data may be restricted to the diagnostically relevant area of the jaw region with very little effort. Equally, a signal from anatomical structures outside of the diagnostically relevant area of the jaw region may be advantageously manipulated by emitting a saturation pulse. As a result, the image data of the diagnostically relevant jaw region can be captured with established imaging sequences, and this advantageously simplifies comparability and/or a diagnosis of images of the diagnostically relevant area of the jaw region of different patients.

In a further embodiment, the method also has the following steps:
  providing a representation of the jaw region of the patient as a function of the captured information about the jaw region of the patient by means of an output unit, wherein the representation of the jaw region has at least two regions, which each comprise a partial volume of the jaw region of the patient, wherein at least one region comprises at least part of the diagnostically relevant area,
  capturing an input of a user of the magnetic resonance apparatus, wherein the input of the user comprises a selection of at least one region of the representation of the jaw region of the patient, and
  wherein adjusting the parameter of the magnetic resonance measurement and/or carrying out the magnetic resonance measurement take place as a function of the input of the user.

A representation of the jaw region of the patient can comprise, e.g., a visual mapping of a jaw region or a section of the jaw region. The visual mapping can comprise, for example, a schematic representation of the jaw region, optical image data of the jaw region, and/or a localizer image, which is reconstructed as a function of localizer image data. It is likewise conceivable, however, that the representation of the jaw region of the patient is created on the basis of a magnetic resonance image, an X-ray image, or a model of the jaw region of the patient. The representation of the jaw region has at least one schematic representation of part of an upper dental arch and/or part of a lower dental arch.

The representation of the jaw region is also divided into at least two regions, which each comprise a partial volume of the jaw region of the patient. It is likewise conceivable, however, that the representation of the jaw region is divided into more than two, more than four, more than six regions, etc. At least one region has a diagnostically relevant area of the jaw region of the patient. A region can be taken to mean a partial volume of the jaw region, which comprises at least one section or part of the jaw region. The diagnostically relevant area can be schematically represented, for example as a symbol, a pictogram, a sign, a letter, a number or the like, in the representation of the jaw region. It is also conceivable that the representation of the jaw region comprises image data and/or an image of the jaw region in which the diagnostically relevant area is segmented and/or marked. In an embodiment, the representation of the jaw region of the patient is configured as part of a graphical user interface, which enables an interaction with a user of the magnetic resonance apparatus.

For example, capturing the input of the user cam comprise selection of a region by the user. For this, the user can select the region by means of any desired input unit such as a mouse, a keyboard, a touchscreen, and the like, on the graphical user interface. It is also conceivable that capturing the input of the user comprises a selection of a plurality of regions of the representation of the jaw region. In an embodiment, at least one region of the selected regions contains the diagnostically relevant area of the jaw region of the patient.

Adjusting the parameter of the magnetic resonance measurement and/or carrying out the magnetic resonance measurement may take place as a function of the selected region or the selected regions. This can mean that an imaging volume of the magnetic resonance measurement is adjusted such that it matches the region or regions selected by the user. It is likewise conceivable that a volume of the jaw region, which is excited by means of the excitation pulse, matches by means of the selected region and/or the selected regions.

In one embodiment, a compensation volume is ascertained as a function of the selected region or the selected regions, which volume surrounds the selected region or the selected regions. The compensation volume can be greater than a volume determined by the selected region or selected regions and surround it/them. In an embodiment, the compensation volume is determined by means of a safety factor, which is multiplied by a volume of the selected region or the selected regions. Adjusting the parameter of the magnetic resonance measurement and/or carrying out the magnetic resonance measurement can accordingly take place as a function of the compensation volume. By using a compensation volume, cropping of part of the diagnostically relevant area of the jaw region as a consequence of a movement of the patient, but also an occurrence of convolution artifacts and/or an incorrect registering of image data and/or images with the captured image data may advantageously be reduced or prevented.

By capturing the input of the user in respect of the selection of regions, from which image data is too be captured, the diagnostically relevant area may advantageously be expanded by regions, which the user regards as relevant to a diagnosis. Furthermore, implementation of the magnetic resonance measurement may in the short term also widen to those regions in which a diagnostic relevance is unclear. This can be the case if further regions with diseases are identified when capturing the optical image data and/or the localizer image data.

According to one embodiment of the method, adjusting the parameter of the magnetic resonance measurement comprises determining a desired position of an antenna element as a function of the captured information about the jaw region and/or the input of the user, also having the following step:

positioning the antenna element at the jaw region of the patient as a function of the desired position, wherein carrying out the magnetic resonance measurement comprises capturing image data of the jaw region of the patient by means of the positioned antenna element.

As described above, a dental coil can be used for capturing the image data of the jaw region. It is conceivable that the dental coil has flexible elements for an orientation of antenna elements and/or can be positioned at different positions of a dental arch of the patient. In such embodiments of the dental coil the antenna elements can be positioned as a function of the captured information about the jaw region and/or the input of the user. In an embodiment, a desired position of an antenna element or a plurality of antenna elements is determined for this as a function of the captured information about the jaw region and/or the input of the user. The desired position of an antenna element or the plurality of antenna elements can be determined as a function of receiving profiles of individual antenna elements of the dental coil, which are stored, for example, on a memory unit of the magnetic resonance apparatus and/or are determined by means of reference measurements.

The positioning of the antenna element or the plurality of antenna elements can be carried out automatically, by remote control, or manually by the user. With manual positioning by the user, e.g. a schematic representation can be output on an output unit of the magnetic resonance apparatus, which can be used by the user as a template or as guidance. It is likewise conceivable, however, that the dental coil has a drive, which positions the antenna element or the plurality of antenna elements at the jaw region as a function of the desired position automatically or by remote control. The image data of the jaw region of the patient can accordingly be captured by means of the positioned antenna element.

By positioning an antenna element at the jaw region as a function of the captured information about the jaw region of the patient, a receiving volume of one or more antenna element(s) may be coordinated with the diagnostically relevant area and/or with a region selected by the user. As a result, a signal-to-noise ratio of the captured image data and/or a quality of the captured image data of the jaw region of the patient may advantageously be increased.

According to a further embodiment of the method, the image data of the jaw region is captured with a plurality of antenna elements, wherein reconstructing the image of the diagnostically relevant area of the jaw region comprises a weighting of image data of the plurality of antenna elements, wherein image data of areas outside of the diagnostically relevant area of the jaw region of the patient are weighted to a lesser extent.

It is conceivable that image data of a volume outside of the diagnostically relevant area of the jaw region is separated or faded out when weighting the image data of the plurality of antenna elements. Image data, which has at least part of the diagnostically relevant jaw region, can be weighted as a function of a position relative to the diagnostically relevant jaw region and/or a relative portion of the diagnostically relevant jaw region in the image data. A weighting can comprise, e.g., adjusting a contrast and/or a transparency of a pixel of the reconstructed image of the diagnostic jaw region of the patient.

By weighting image data of the plurality of antenna elements, anatomical structures of the jaw region, which are located outside of the diagnostically relevant area, may be faded out and/or deemphasized from the image of the diagnostically relevant jaw region with very little effort. As a result, the attention of the user may advantageously be focused on the diagnostically relevant area of the jaw region.

According to a further embodiment of the method, capturing the image data of the jaw region comprises capturing image data of an anatomical structure outside of the jaw region of the patient, wherein reconstructing the image of the jaw region of the patient comprises identifying the anatomical structure in the image of the diagnostically relevant area of the jaw region of the patient, and wherein the identified anatomical structure is faded out in the image of the diagnostically relevant area of the jaw region of the patient.

Even after adjusting a parameter of the magnetic resonance measurement according to an above-described embodiment even further anatomical structures of the patient can be present in the image of the diagnostically relevant area of the jaw region. It is conceivable that the computing unit of the magnetic resonance apparatus has an image processing algorithm, which identifies anatomical structures in the image of the diagnostically relevant jaw region of the patient. Such identifying can comprise, for example, segmenting and/or marking of such anatomical structures in the image of the diagnostically relevant jaw region of the patient. It is conceivable that a contrast or a gray scale of a pixel of an identified anatomical structure is changed to fade out the identified anatomical structure from the image of the diagnostically relevant jaw region. The gray scale of the pixel can be adjusted such that the gray scale differs from a gray scale of the nearest pixel, which may be assigned to the diagnostically relevant area of the jaw region. The gray scale of the pixel can assume, e.g., a minimum value or a maximum value during adjusting. It is likewise conceivable, however, that a transparency of pixels of identified anatomical structures is adjusted in order to fade out the identified anatomical structure.

By fading out anatomical structures, which are located outside of the diagnostic area of the jaw region of the patient, the risk of a misdiagnosis as a consequence of a misinterpretation of the image of the diagnostically relevant area may advantageously be reduced or prevented. A misinterpretation of this kind can occur, e.g., due to an overlaying of peripheral anatomical structures with an anatomical structure of the diagnostically relevant area, which are difficult for users without radiological expertise to assess.

In a further embodiment of the method, reconstructing the image of the diagnostically relevant area of the jaw region takes place as a function of the model of the jaw region, wherein image data of areas outside of the diagnostically relevant area of the jaw region of the patient are faded out as a function of the model.

The model of the jaw region can be configured according to an embodiment described above. In an embodiment, anatomical structures of captured image data of the diagnostically relevant area of the jaw region are registered with corresponding anatomical structures of the model of the jaw region when reconstructing the image of the diagnostically relevant area of the jaw region. Captured image data with anatomical structures outside of the diagnostically relevant area of the jaw region can be separated or faded out in the process. The diagnostically relevant area of the jaw region may already be registered according to an embodiment described above with the model of the jaw region, so the captured image data can be compared or aligned with the model of the jaw region when reconstructing the image of the diagnostically relevant area of the jaw region.

By registering anatomical structures of the captured image data with the model of the jaw region of the patient, the image of the diagnostically relevant area of the jaw region may be limited to the diagnostically relevant area of the jaw region with little effort. At the same time, when registering the captured image data with the model of the jaw region an effect of a movement of the patient during the magnetic resonance measurement can be compensated or corrected. As a result, a repetition of the magnetic resonance measurement can be advantageously avoided in the case of movement of the patient.

In one embodiment of the method, capturing the information about the jaw region, adjusting the parameter of the magnetic resonance measurement, and/or reconstructing the image of the diagnostically relevant area of the jaw region takes place as a function of an intelligent algorithm.

An intelligent algorithm can comprise an artificial neural network, a multi-layer neural network, an optimization method, an expert system, or the like. For example, the intelligent algorithm can be designed to determine information about the jaw region of the patient as a function of optical image data of the set of teeth, an X-ray image, a magnetic resonance image and/or localizer image data of the jaw region of the patient and/or to undertake adjusting of a parameter of the magnetic resonance measurement. It is likewise conceivable that the intelligent algorithm is designed to optimize a parameter or a plurality of parameters of the magnetic resonance measurement as a function of the information about the jaw region of the patient. Furthermore, the intelligent algorithm can be designed to carry out the image of the diagnostically relevant area of the jaw region of the patient as a function of the information about the jaw region of the patient.

Use of an intelligent algorithm allows partial steps of the inventive method to be automated. Furthermore, application of an intelligent algorithm enables a particularly time-efficient and/or robust progression of the inventive method. For instance, use of an intelligent algorithm allows optimum positioning of an imaging volume or a plurality of imaging volumes to be achieved. As a result, a duration of the magnetic resonance measurement can be reduced and/or the quality of the provided image of the diagnostically relevant area of the jaw region of the patient can be advantageously increased.

The magnetic resonance apparatus comprises a computing unit, wherein the computing unit is designed to coordinate a method as claimed in one of the preceding claims and carry it out by means of the magnetic resonance apparatus.

For capturing, processing, and storing data, such as a parameter of the magnetic resonance measurement, an imaging parameter, captured information about the jaw region of the patient, a reference to a position, and/or an extent of a diagnostically relevant area of a jaw region, captured image data of the jaw region and the like, the magnetic resonance apparatus can have further components apart from the computing unit. For example, the magnetic resonance apparatus can comprise a control unit, a main memory, a memory unit, and a suitable interface for the input and output of data. The computing unit can comprise, for example, a controller, a microcontroller, a CPU, a GPU or the like. The main memory and the memory unit can have memory technologies, such as RAM, ROM, PROM, EPROM, EEPROM, Flash memory, but also HDD memories, SSD memories or the like. It is conceivable that the memory unit comprises an internal database, which is electrically and/or mechanically connected to the computing unit of the magnetic resonance apparatus. It is likewise conceivable, however, that the memory unit is an external database, which is connected by means of a network connection to the computing unit. Examples of external memory units are network servers with appropriate data memories and a memory unit of a Cloud. The data can be transferred by means of analog and/or digital signals and suitable wired and/or wireless signal links between the components of the magnetic resonance apparatus. For an interaction with a user, such as outputting a representation of the jaw region and/or capturing an input of a user, the magnetic resonance apparatus can also comprise an input unit and an output unit as further components.

The computing unit may be electrically connected to a control unit of the magnetic resonance apparatus and/or integrated in the control unit. The control unit can be configured to carry out, with coordination by the computing unit, a method according to an embodiment described above. The control unit can be configured, e.g., to carry out a magnetic resonance measurement of a jaw region of a patient, to capture image data of the jaw region of the patient, and to transfer the captured image data to other components, such as the computing unit, the memory unit, and/or an output unit. Furthermore, the control unit described can be designed to adjust parameters of the magnetic resonance measurement with coordination by the computing unit.

The computing unit can be configured to ascertain an adjustment of a parameter of the magnetic resonance measurement as a function of information about the jaw region of the patient and/or the input of the user. The computing unit can also be designed to process the input of the user with a selection of a region or a plurality of regions of a representation of the jaw region. The input of the user may be captured by means of the input unit of the magnetic resonance apparatus. The input unit can be a stand-alone component of the magnetic resonance apparatus or be integrated in the magnetic resonance apparatus.

The components of the magnetic resonance apparatus can be advantageously matched to each other, enabling a time-efficient and robust implementation of a method. For instance, the magnetic resonance apparatus can be designed to autonomously coordinate and carry out the progressions of individual method steps. The adjustment of a parameter of the magnetic resonance measurement as a function of the information about the jaw region the patient can thus advantageously be carried out automatically and/or without technical expertise of the user.

A computer program product is provided, which can be loaded directly into a memory unit of a computing unit of an magnetic resonance apparatus, with program code means to carry out a method according to an embodiment described above when the computer program product is run in the computing unit of the magnetic resonance apparatus.

The method can be carried out quickly, in an identically repeatable manner, and robustly by way of the computer program product. The computer program product is configured such that it can carry out the method steps by means of the computing unit. The computing unit has in each case suitable hardware, such as an appropriate main memory, an appropriate graphics card or an appropriate logic unit, so the respective method steps can be efficiently carried out. The computer program product is stored, for example, on a computer-readable medium or saved on a network, a server, or the cloud from where it can be loaded into a processor of the computing unit. The computing unit can be designed as a stand-alone system component or as part of the magnetic resonance apparatus. Furthermore, control information of the computer program product can be stored on an electronically readable data carrier. The control information of the electronically readable data carrier can be configured in such a way that it carries out a method when the data carrier is used in the computing unit of the magnetic resonance apparatus. Examples of electronically readable data carriers are a DVD, a magnetic tape, a USB stick, or any other suitable data memory on which electronically readable control information, e.g. software, is stored. When this control information is read from the data carrier and transferred to a control unit and/or the computing unit of the magnetic resonance apparatus, all embodiments of the described methods can be carried out.

BRIEF DESCRIPTION OF THE DRAWINGS/FIGURES

Further advantages and details of the present disclosure can be found in the exemplary embodiments described below and with reference to the drawings, in which:

FIG. 1 shows an embodiment a magnetic resonance apparatus, in accordance with one or more embodiments of the present disclosure;

FIG. 2 a schematic representation of a diagnostically relevant area of a jaw region, in accordance with one or more embodiments of the present disclosure;

FIG. 8 shows one possible flowchart of a method, in accordance with one or more embodiments of the present disclosure.

DETAILED DESCRIPTION

Figure 1:
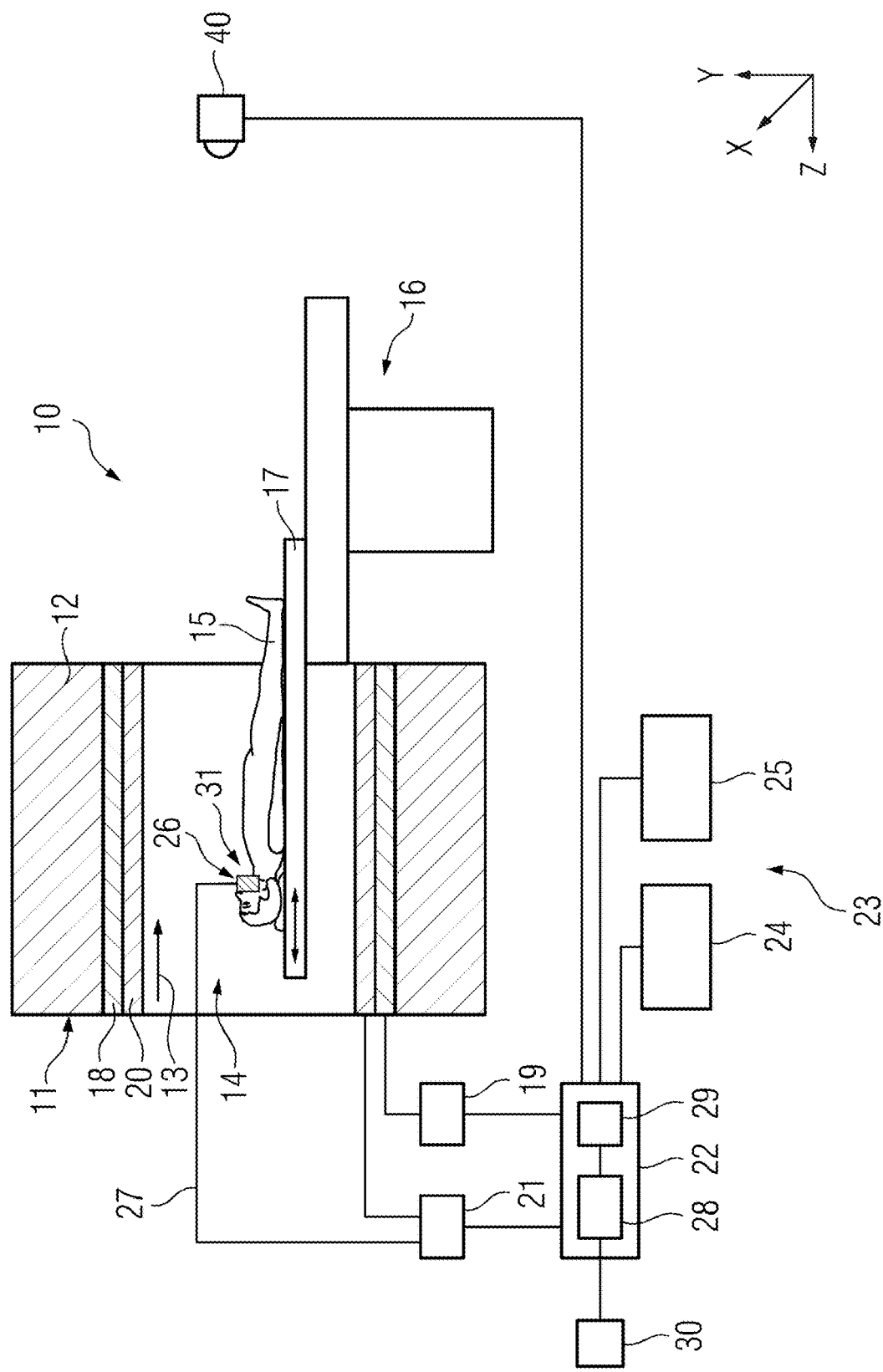

FIG. 1 shows an embodiment of the magnetic resonance apparatus 10. The magnetic resonance apparatus 10 comprises a magnetic unit 11, which has for example, a permanent magnet, an electromagnet, or a superconducting main magnet 12 for the generation of a strong and homogeneous main magnetic field 13 (B0 magnetic field). In addition, the magnetic resonance apparatus 10 comprises a patient-receiving area 14 for receiving a patient 15. In the present exemplary embodiment, the patient-receiving area 14 is cylindrical and surrounded in a circumferential direction by the magnetic unit 11. Designs of the patient-receiving area 14 that differ from this example are also conceivable, however.

The patient 15 can be positioned in the patient-receiving area 14 by means of a patient positioning apparatus 16 of the magnetic resonance apparatus 10. The patient positioning apparatus 16 has for this purpose a patient couch 17 configured to move inside the patient-receiving area 14. The magnetic unit 11 also has a gradient coil 18 for generating magnetic gradient fields, which is used for spatial encoding during a magnetic resonance measurement. The gradient coil 18 is actuated by means of a gradient control unit 19 of the magnetic resonance apparatus 10. The magnetic unit 11 can also comprise a radio-frequency antenna, which in the present exemplary embodiment is designed as a body coil 20 permanently integrated in the magnetic resonance apparatus 10. The body coil 20 is configured for excitation of nuclear spins, which are in the main magnetic field 13 generated by the main magnet 12. The body coil 20 is actuated by a radio-frequency unit 21 of the magnetic resonance apparatus 10 and irradiates radio-frequency excitation pulses into an image acquisition region, which is formed substantially by a patient-receiving area 14 of the magnetic resonance apparatus 10. The body coil 20 is also designed to receive magnetic resonance signals and can be a receiving unit of the magnetic resonance apparatus 10.

The magnetic resonance apparatus 10 has a control unit 22 to control the main magnet 12, the gradient control unit 19, and to control the radio-frequency unit 21. The control unit 22 is designed to control implementation of an imaging sequence of the imaging examination, such as a GRE (gradient echo) sequence, a TSE (turbo spin echo) sequence, or a UTE (ultra-short echo time) sequence. In addition, the control unit 22 comprises a computing unit 28 for evaluation of magnetic resonance signals, which are detected during a magnetic resonance measurement. The computing unit 28 of the magnetic resonance apparatus 10 can be designed to carry out a correction method to reduce an effect of a movement of a diagnostically relevant body region 31 of the patient 15 on the magnetic resonance measurement.

Furthermore, the magnetic resonance apparatus 10 comprises a user interface 23, which has a signal link to the control unit 22. Control information, such as imaging parameters of the magnetic resonance measurement, but also a reconstructed image of the diagnostically relevant area 32 of the jaw region 31 and/or a representation of the jaw region 33, can be displayed for a user on an output unit 24, for example on at least on monitor, of the user interface 23. The output unit 24 can be configured, e.g., to provide a graphical user interface with the representation of the jaw region 33. Furthermore, the user interface 23 has an input unit 25 by means of which parameters of a magnetic resonance measurement can be input by the user. The input unit can be configured, in particular, to enable a selection of one or more region(s) 35 of the representation of the jaw region 33 by the user.

In the present example, the computing unit 28 is connected to a memory unit 29 of the magnetic resonance apparatus 10. Optionally, the computing unit 28 can also be connected to the cloud 30. The computing unit 28 can be configured to store data, such as optical image data, localizer image data, magnetic resonance images, X-ray images or the like, on the memory unit 29 and/or the cloud 30 and/or to retrieve data from the memory unit 29 and/or the cloud 30 by means of a suitable interface (not shown). It is conceivable in particular that the cloud 30 is designed to receive captured image data and/or images from the magnetic resonance apparatus 10 and to carry out registering of image data and/or images. The cloud 30 can also be designed to adjust a model of a jaw region 31 as a function of the captured image data and/or images but also a correction method as a function of the model of the jaw region 31. In an embodiment, the cloud 30 is also designed to transfer a result to the computing unit 28. Of course, the computing unit 28 can also be designed to carry out a registration of image data and/or images, adjusting of the model of the jaw region 31, and/or a correction method.

The magnetic resonance apparatus 10 can also have a dental coil 26, which is positioned in a position appropriate to the application on the diagnostically relevant area 32 of the jaw region 31 of the patient 15. The dental coil 26 may have a plurality of antenna elements (not shown), which detect magnetic resonance signals of the diagnostically relevant area 32 of the jaw region 31 of the patient 15 and transfer them to the computing unit 28 and/or the control unit 22. In the present case, the dental coil 26 has an electrical connection line 27, which provides a signal link to the radio-frequency unit 21 and the control unit 22. Just like the body coil 20, the dental coil 26 can also be designed for exciting nuclear spins in the jaw region 31 of the patient 15. The dental coil 26 can be actuated by the radio-frequency unit 21 for this purpose. In one example, the dental coil 26 is designed as a mask, which is positioned in a position appropriate to the application on a main surface of the jaw region 31 of the patient 15. It is likewise conceivable, however, that the dental coil 26 is mechanically connected to a night guard, which is positioned in a position appropriate to the application on a dental arch of the patient 15.

The magnetic resonance apparatus 10 can also have a camera 40, such as a 2D camera, a 3D camera, an infrared camera, or the like. The camera 40 may be designed (i.e. configured) to capture optical image data of a set of teeth of the patient 15. For capturing optical image data, the patient 15 can be positioned in front of the camera 40 before positioning in the patient-receiving area 14. It is likewise conceivable, however, that the camera 40 is positioned in the patient-receiving area 14. The camera 40 can be connected, for example, to the dental coil 26 or a head coil (not shown).

The illustrated magnetic resonance apparatus 10 can of course comprise further components, which magnetic resonance apparatuses conventionally have. It is likewise conceivable that instead of the cylindrical construction, the magnetic resonance apparatus 10 has a C-shaped, a triangular or an asymmetrical structure of the magnetic field-generating components. The magnetic resonance apparatus 10 can e.g. be designed to carry out a magnetic resonance measurement of a standing or seated patient 15.

Figure 2:
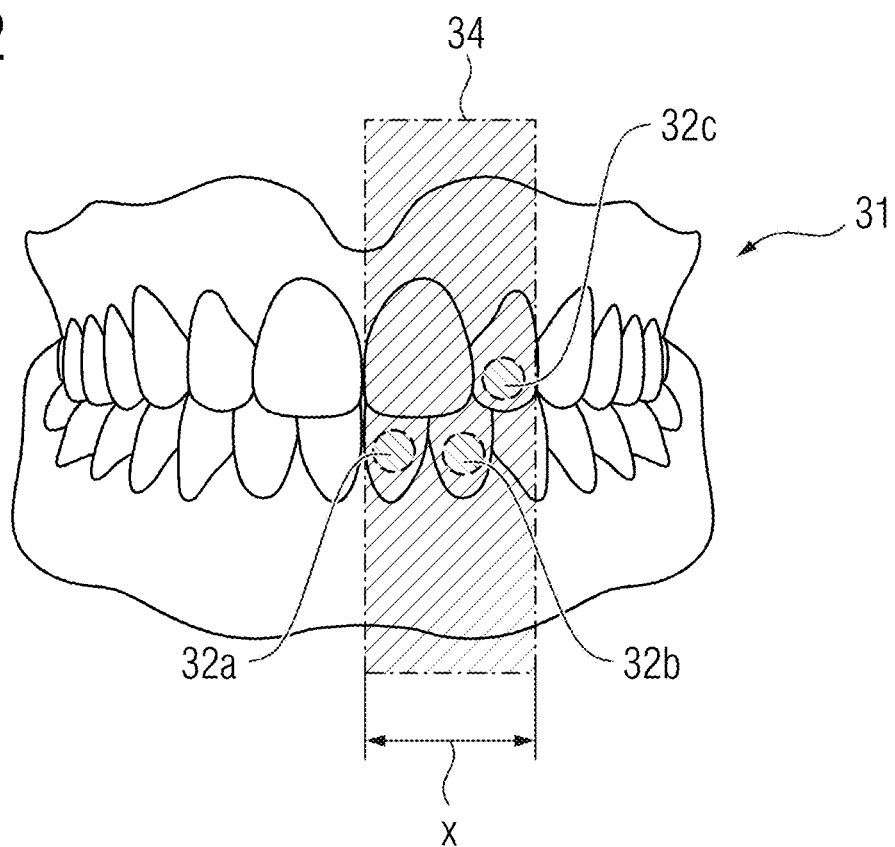

FIG. 2 shows a representation of a plurality of diagnostically relevant areas 32*a*, 32*b*, and 32*c* (32*a-c*) of a jaw region 31 of the patient 15. It is conceivable that the representation of the jaw region 31 in FIG. 2 is created as a function of optical image data, which is captured by means of the camera 40 during preparation of the patient 15 for the magnetic resonance measurement. The schematic representation of the jaw region 31 can likewise be a simplified representation of the jaw region 33, however, which is provided to the user by means of the output unit 24. The diagnostically relevant areas 32*a-c* can represent for example teeth or sections of teeth with dental caries and/or adjoining gingivitis. As illustrated in FIG. 2, the diagnostically relevant areas 32*a-c* can be positioned relatively close to each other. In the present example, the imaging volume 34 is adjusted in such a way that all diagnostically relevant areas 32*a-c* are encompassed by the imaging volume 34. Apart from the adjustment of a width X of the imaging volume 34 along a plane oriented parallel to a frontal plane of the patient 15, the imaging volume 34 can of course also be adjusted along a depth Y (not shown), which is oriented parallel to a sagittal plane of the patient 15, to the diagnostically relevant areas 32*a-c*. The imaging volume 34 can also comprise roots of the teeth with the diagnostically relevant areas 32*a-c*.

Figure 3:
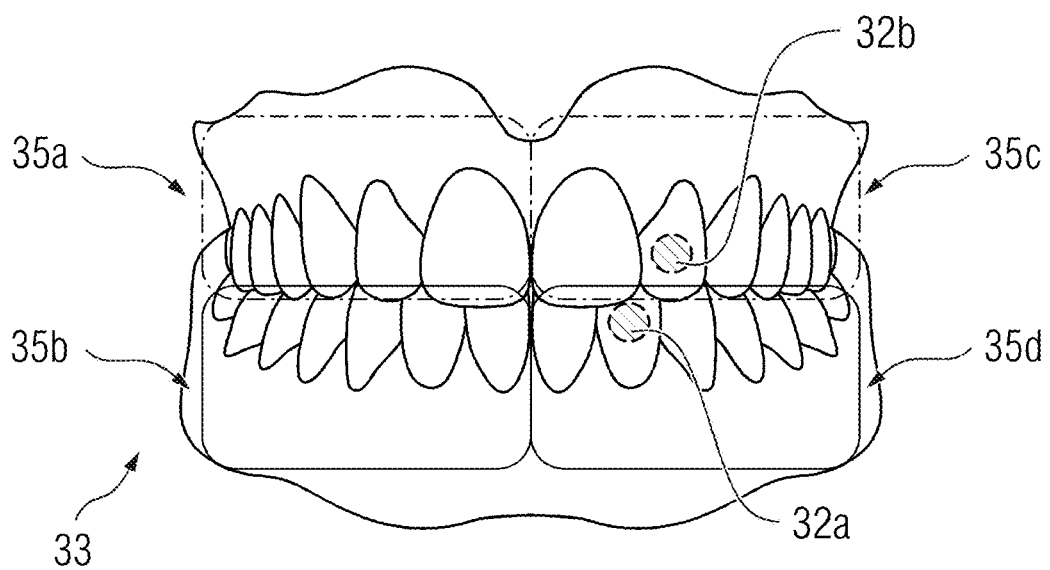
FIG. 3 shows a schematic representation of a presentation of a jaw region, in accordance with one or more embodiments of the present disclosure.

FIG. 3 shows a schematic representation of a presentation of a jaw region 33, which in the present case is divided into the regions 35*a*, 35*b*, 35*c*, and 35*d* (35*a-d*). The representation of the jaw region 33 is provided to the user of the magnetic resonance apparatus 10 as part of a graphical user interface by means of the output unit 24. It is conceivable that the individual regions 35*a-d* can be selected by means of the input unit 25 to determine the imaging volume 34 of the magnetic resonance measurement. In the present example, the user can select, for example, the regions 35*c* and 35*d* to carry out a magnetic resonance measurement of the diagnostically relevant areas 32*a* and 32*b*. Of course, the representation of the jaw region 33 can also be discretized or divided into a smaller or greater number of regions 35, enabling a rougher or finer coordination of the imaging volume 34 with diagnostically relevant areas 32 of the jaw region 31. Furthermore, a position of an antenna element and/or a weighting of antenna elements can also be influenced as a function of the regions 35*a-d*. The regions 35 of the representation of the jaw region 33 can comprise separate partial volumes of the jaw region 31, or partially overlap.

Figure 4:
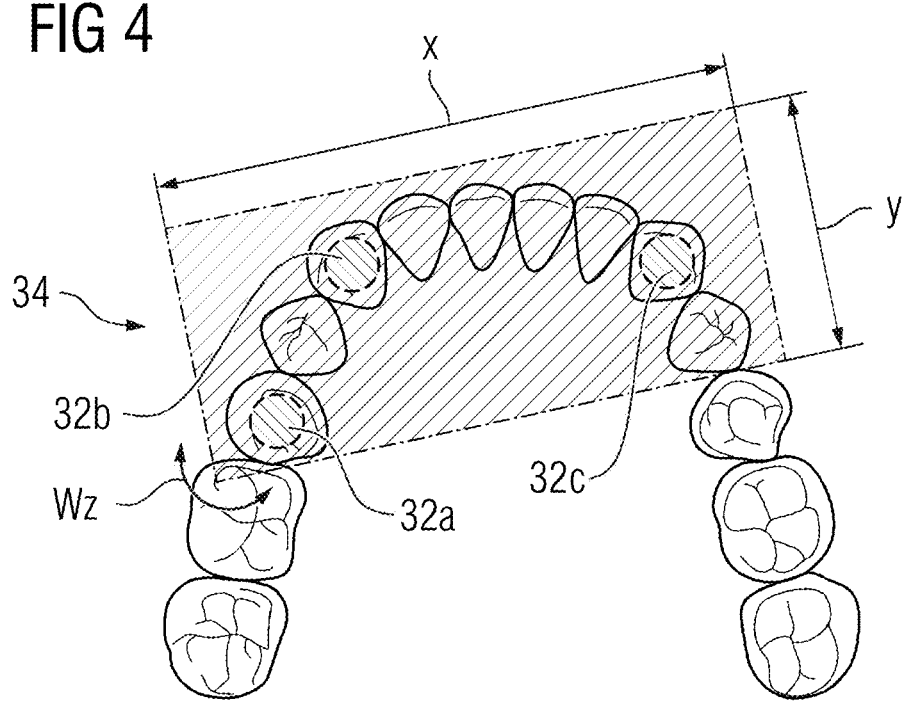
FIG. 4 shows a schematic representation of a diagnostically relevant area of a jaw region, in accordance with one or more embodiments of the present disclosure.

FIG. 4 shows a further example of a schematic representation of the diagnostically relevant area 32 of the jaw region 31. A lower dental arch of the patient 15 is illustrated by means of a visualization of a model of the jaw region 31 of the patient 15. The model of the jaw region 31 is also registered with the diagnostically relevant areas 32*a-c*. In an embodiment, the model of the jaw region 31 of the patient 15 is adjusted as a function of information about the jaw region 31 in such a way to the jaw region 31 of the patient 15 that a relative position between teeth and/or a relative size ratio of the teeth substantially matches an arrangement of the teeth of the jaw region 31 of the patient 15.

The imaging volume 34 of the magnetic resonance measurement is substantially restricted to the diagnostically relevant area 32*a-c* of the jaw region 31 of the patient. It is conceivable that the imaging volume 34 is adjusted along the X-direction, the Y-direction, the Z-direction (not shown), but also the direction of rotation Wz and/or further directions of rotation in such a way that a portion of anatomical structures outside of the diagnostically relevant areas 32*a-c* is reduced or minimized in the imaging volume 34.

It is conceivable that a representation of the diagnostically relevant area 32 according to FIG. 4 is output as a representation of the jaw region 33 by means of the output unit 24 to the user. The representation of the jaw region 33 is divided for this purpose into regions 35, which can be selected by the user by means of the input unit 25.

Figure 5:
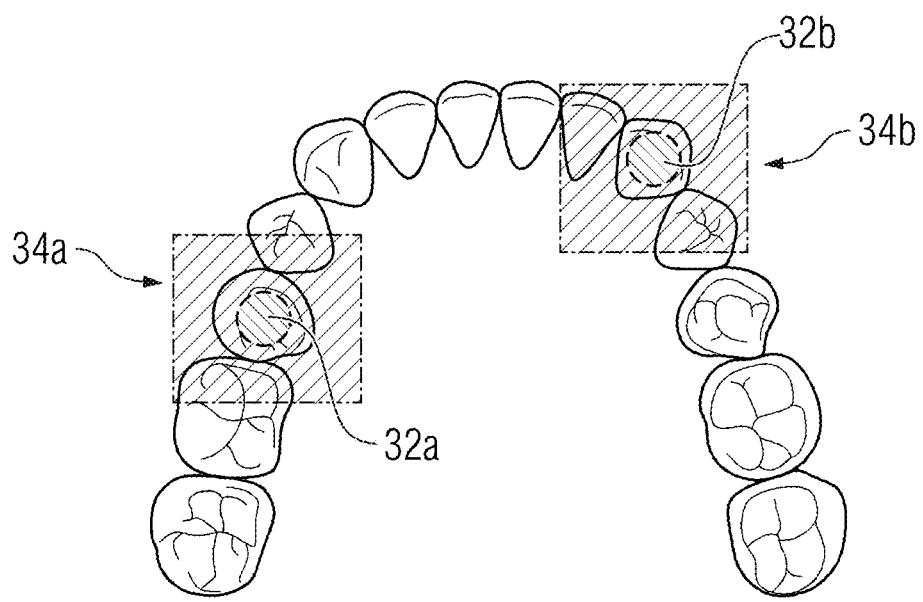
FIG. 5 shows a schematic representation of a presentation of a jaw region, in accordance with one or more embodiments of the present disclosure.

FIG. 5 shows a further schematic representation of the diagnostically relevant area 32 of the jaw region 31. In the example shown, the two diagnostically relevant areas 32*a* and 32*b* are spaced so far apart from each other that the image data of the diagnostically relevant areas 32*a* and 32*b* is captured by means of two imaging sequence with separate or unconnected imaging volumes 34*a* and 34*b*. Compared to the example shown in FIG. 4, the images of the magnetic resonance measurement may be restricted even further to the diagnostically relevant areas 32*a* and 32*b* by means of separation of the imaging volume in the present example. The division of the imaging volumes 34*a* and 34*b* illustrated in FIG. 5 should be understood as being exemplary. The imaging volumes 34*a* and 34*b* can of course turn out to be larger or smaller and/or have a different orientation. For example, an imaging volume 34*a* could cover a row of adjacent teeth, which run parallel to a sagittal or a frontal plane of the patient.

Figure 6:
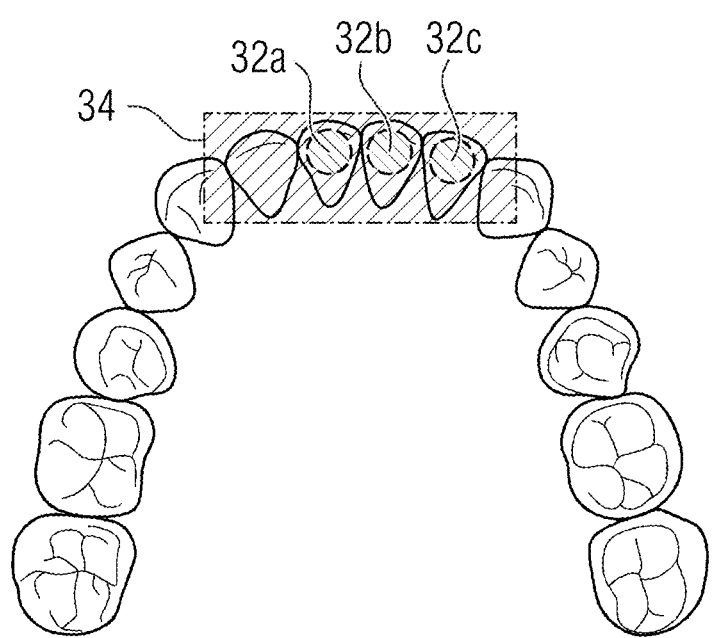
FIG. 6 shows a schematic representation of a presentation of a jaw region, in accordance with one or more embodiments of the present disclosure.

In FIG. 6, the diagnostically relevant areas 32*a*, 32*b* and 32*c* (32*a-c*) are positioned by way of example at the front teeth of the lower jaw of the patient 15. During the magnetic resonance measurement, the plurality of individual slices can be oriented parallel to the frontal plane of the patient 15 and substantially cover a volume of the front teeth of the lower jaw. A second imaging volume 34*b* (not shown) could by contrast cover at any further diagnostically relevant area 32 or partially overlap with the imaging volume 34*a*.

Figure 7:
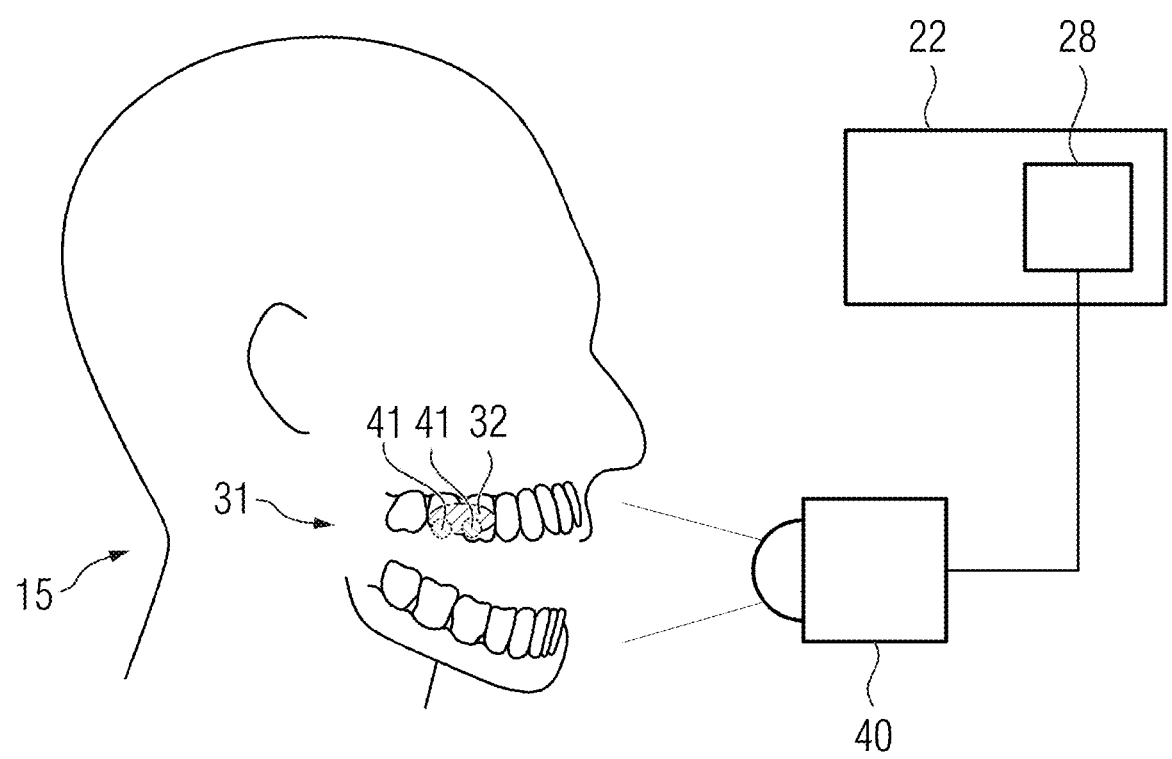
FIG. 7 shows an embodiment of a magnetic resonance apparatus, in accordance with one or more embodiments of the present disclosure.

FIG. 7 shows an embodiment of the magnetic resonance apparatus 10 in which for acquisition of optical image data of the set of teeth of the patient 15 the camera 40 is positioned in front of the jaw region 31 of the patient 15. The patient 15 may open their mouth so the camera 40 can capture optical image data of the set of teeth. A diagnostically relevant area 32 can be marked, for example with an optical marker 41, to simplify identifying of the diagnostically relevant area 32 of the jaw region 31. It is also conceivable that instead of or in addition to the optical marker, a magnetic resonance-active marker is used, which may be identified for example in localizer image data of a localizer measurement. Use of an optical marker and a magnetic resonance-active marker (or a combined optical and magnetic resonance-active marker) enables the optical image data to be advantageously registered with the localizer image data as a function of the positions of the optical marker and of the magnetic resonance-active marker.

FIG. 8 shows one possible flowchart of a method for providing an image of a diagnostically relevant area 32 of a jaw region 31 of a patient 15 by means of a magnetic resonance apparatus 10.

In a step S1, information about the jaw region 31 of the patient 15 is captured, with the information about the jaw region 31 comprising at least one reference to a position and/or an extent of the diagnostically relevant area 32 of the jaw region 31.

The information about the jaw region 31 of the patient can be, for example, a diagnostic finding, which can contain information about a disease, a progress stage of a disease and an affected anatomical structure of the jaw region 31 of the patient 15. It is likewise conceivable, however, that the information about the jaw region 31 comprises image data and/or an image (see for example FIG. 2) of the jaw region 31, which is captured by means of a camera 40 and/or the magnetic resonance apparatus 10. It is also conceivable that corresponding image data and/or images are retrieved from a memory unit 29, a memory unit of the Cloud 30 and/or a medical information system. In an embodiment, the computing unit 28 has an image processing unit, which ascertains the position and/or the extent of the diagnostically relevant area 32 of the jaw region 31 of the patient 15 on the basis of the image data and/or of the image.

In one embodiment, capturing the information about the jaw region 31 of the patient 15 comprises capturing optical image data of a set of teeth of the patient 15, an X-ray image of the jaw region 31 of the patient 15, a magnetic resonance image of the jaw region 31 of the patient 15, and/or localizer image data and/or an image of a localizer measurement of the jaw region 31 of the patient 15.

Optical image data of the patient 15 can be captured, for example, by means of the camera 40. In an embodiment, the optical image data, as shown in FIG. 2, comprises at least image data of a tooth of the patient 15. It is likewise conceivable that capturing the information about the jaw region 31 of the patient comprises carrying out a localizer measurement by means of the magnetic resonance apparatus 10. A diagnostically relevant area 32 of the jaw region can be marked with a magnetic resonance-active marker, such as encapsulated Vitamin D or cod liver oil, to simplify identifying of the diagnostically relevant jaw region 31. Furthermore, an optical marker can be used, which can be identified for example by means of the image processing unit on the basis of the optical image data. In addition, images of a preceding X-ray examination and/or a preceding magnetic resonance examination can of course also be captured. Such X-ray images and/or magnetic resonance images may be registered with optical image data, localizer image data, and/or a model of the jaw region 31 of the patient 15 to assist a localization of diagnostically relevant areas 32 of the jaw region 31, and/or to simplify adjusting of a parameter of the magnetic resonance measurement or make it more precise.

In one embodiment, capturing information about the jaw region 31 of the patient 15 also comprises ascertaining a relative position of a first anatomical structure of the jaw region 31 of the patient 15 and a second anatomical structure of the jaw region 31 of the patient 15. A first anatomical structure can be, for example, a front tooth of the patient 15 while the second anatomical structure is a lower jawbone of the patient. In an embodiment, the relative position of the front tooth and of the lower jawbone is ascertained as a function of optical image data of the set of teeth of the patient 15, of localizer image data of the jaw region 31 and/or of the model of the jaw region 31 by means of the computing unit 28. For example, the front tooth of the patient 15 has a diagnostically relevant area 32, such as dental caries and/or a growth deformity. It is conceivable that a localization of the front tooth and/or an adjustment of a parameter of the magnetic resonance measurement may be simplified or made more precise with knowledge of a relative position between the front tooth and the lower jaw of the patient 15. Knowledge of the relative position between the front tooth and the lower jaw of the patient 15 can be relevant in particular for a determination of an imaging volume 34 as a function of a simplified model of the jaw region 31 in which no positions of individual teeth or other anatomical structures are resolved.

In a further example, capturing the information about the jaw region 31 of the patient 15 comprises capturing localizer image data of the jaw region 31 of the patient 15 by means of the magnetic resonance apparatus 10, wherein as a function of the localizer image data a plurality of individual slices is determined in the diagnostically relevant area 32 of the jaw region 31. The plurality of individual slices can, as shown in FIG. 5, constitute separate imaging volumes 34a and 34b. It is likewise conceivable, however, that the plurality of individual slices constitute a shared imaging volume 34, which is adjusted to a position and/or an extent of the diagnostically relevant area of the jaw region. In an embodiment, the imaging volume is divided into a plurality of individual slices as a function of overshooting of a predetermined characteristic number, which for example is characterized, for example, by a ratio of an extent of a first diagnostically relevant area 32a to a spacing between the first diagnostically relevant area 32a and a second diagnostically relevant area 32b.

In an optional step S2, a model of the jaw region 31 of the patient 15 is adjusted as a function of the captured information about the jaw region 31 of the patient 15. The model can comprise information about a structural composition of the jaw region 31 of the patient 15 and be configured to reconstruct or ascertain mechanical or a biomechanical behavior of the jaw region 31 of the patient 15. In an embodiment, the model of the jaw region 31 of the patient 15 is adjusted starting from a generic or statistical body model or jaw model, which is retrieved, for example, from a memory unit 29 or the cloud 30. Adjusting the model of the jaw region 31 can comprise, e.g., registering and/or aligning anatomical structures of the model with corresponding anatomical structures of the jaw region 31 as a function of image data and/or an image by means of the computing unit 28.

In an optional step S3, a representation of the jaw region 33 of the patient 15 is provided as a function of the captured information about the jaw region 31 of the patient 15 by means of an output unit 24, with the representation of the jaw region 33 being divided into at least two regions 35a and 35b, which each comprise a partial volume of the jaw region 31 of the patient 15, wherein at least one region 35a comprises at least part of the diagnostically relevant area 32.

It is conceivable that the representation of the jaw region 33 is divided as a function of a number of identified diagnostically relevant areas 32 into a number of regions 35. This can mean that the number of regions 35 correlates with a number of diseased teeth and/or sites of inflammation on the gums of the jaw region 15. The manner of the division into regions 35, such as a shape of individual regions 35 and/or a distribution of regions 35 over a volume of the jaw region 31, can be determined in particular by means of an image processing unit of the computing unit 28 as a function of optical image data and/or localizer image data of the jaw region of the patient 15.

The optional step S3 may be followed by optional step S4 in which an input of a user of the magnetic resonance apparatus 10 is detected, with the input of the user comprising a selection of at least one region 35 of the representation of the jaw region 33 of the patient 15.

The input of the user may be detected by means of the input unit 25. For this purpose, the user can select, for example, individual regions 35a and 35b of the representation of the jaw region 33 by means of a mouse, a touchscreen and/or a keyboard on a graphical surface of the output unit 24. An imaging volume or a volume relevant to the magnetic resonance measurement may be defined by the input of the user and this forms the basis of an adjustment of a parameter of the magnetic resonance measurement, carrying out the magnetic resonance measurement and/or reconstructing an image of the diagnostically relevant area 32 of the jaw region 31 of the patient 15.

In step S5, a parameter of the magnetic resonance measurement is adjusted as a function of the captured information about the jaw region 31 of the patient 15.

The parameter of the magnetic resonance measurement can be adjusted in particular as a function of the model of the jaw region 31, the position of a marker in image data and/or an image of the jaw region 31, the relative position of a first anatomical structure of the jaw region 31 of the patient 15, and a second anatomical structure of the jaw region 31 of the patient 15, the plurality of individual slices and/or the input of the user.

Adjusting the parameter of the magnetic resonance measurement may be used to restrict capturing of image data by means of the magnetic resonance measurement to the diagnostically relevant area 32 or the diagnostically relevant areas 32 of the jaw region 31.

In one embodiment, adjusting the parameter of the magnetic resonance measurement comprises at least:
  adjusting an imaging parameter of the magnetic resonance measurement,
  limiting an imaging volume of the magnetic resonance measurement to the diagnostically relevant area 32, and/or
  adjusting a phase encoding and/or a frequency encoding of the magnetic resonance measurement.

An imaging parameter of the magnetic resonance measurement can be, for example, a slice thickness, a repetition time, an echo time, a spatial resolution, a specific absorption rate or the like. For instance, the imaging parameter can be an imaging volume, which is matched to the position and/or the extent of the diagnostically relevant area 32. In a further example, adjusting the parameter of the magnetic resonance measurement comprise a reduction in a sampling frequency in a phase-encoding direction.

In a further embodiment, adjusting the parameter of the magnetic resonance measurement comprises determining a desired position of an antenna element as a function of the captured information about the jaw region 31 and/or the input of the user. The antenna element may be part of the dental coil 26, which is positioned, for example, on the surface of the skin of the jaw region 31 of the patient 15 or in the oral cavity of the patient 15. It is conceivable that the dental coil 26 and/or individual antenna elements of the dental coil 26 can be positioned relative to the jaw region 31 of the patient 15 in order to match a receiving volume of the dental coil 26 and/or the individual antenna elements to the diagnostically relevant area 32 of the jaw region. Determining the desired position of the antenna element can comprise, e.g., matching the receiving volume of the antenna element to the position and/or the extent of the diagnostically relevant area.

In a further, optional step S6, the antenna element is positioned on the jaw region 31 of the patient 15 as a function of the desired position. It conceivable that the desired position of the antenna element and/or the dental coil 26 is visualized for the user analogously to the representation of the jaw region 33 by means of the output unit 25. It is also conceivable that the desired position of the antenna element is displayed for the user by means of a projection of a representation of the dental coil 26 onto the surface of the skin of the jaw region 31 of the patient 15. The user is guided by means of the visualization to position the dental coil 26 as desired on the jaw region of the patient 15. It is likewise conceivable, however, that the dental coil 26 and/or individual antenna elements are positioned in the desired position on the jaw region 31 of the patient 15 via remote control or automatically by means of an actuator.

In step S7, the magnetic resonance measurement is carried out with the adjusted parameter, with image data of the jaw region 31 of the patient 15 being captured.

In one embodiment, carrying out the magnetic resonance measurement comprises at least:

selecting at least one antenna element from a plurality of antenna elements, with the image data of the jaw region 31 being captured by means of the at least one selected antenna element, selective exciting of the diagnostically relevant area 32 of the jaw region 31 by means of an excitation pulse, and/or saturating nuclear spins in an area outside of the imaging volume 34 by emitting a saturation pulse as a function of the captured information about the jaw region 31.

By selecting the at least one antenna element from the plurality of antenna elements, detecting magnetic resonance signals can be limited to the diagnostically relevant area 32 of the jaw region 31. In an embodiment, magnetic resonance signals of those antenna elements are separated and/or filtered whose receiving profiles are classified as being located outside of the diagnostically relevant area 32 based on the information about the jaw region 31. By separating detected magnetic resonance signals before creating image data, computing capacities of the magnetic resonance apparatus 10 can be advantageously conserved. Selective exciting of the diagnostically relevant area 32 by means of the excitation pulse and/or saturating nuclear spins in an area outside of the imaging volume 34 by means of the saturation pulse can take place e.g. by means of actuating one or more antenna element(s) of the dental coil 26. Appropriate antenna elements can be actuated here by means of the radio-frequency unit 21 of the magnetic resonance apparatus 10, individually or in groups in order to emit excitation pulses and/or saturation pulses into the jaw region 31 of the patient 15.

In further examples, carrying out the magnetic resonance measurement comprises capturing image data of the jaw region 31 of the patient 15 by means of the positioned and/or selected antenna element and/or capturing image data of the plurality of individual slices. The plurality of individual slices can constitute a shared imaging volume 34 or a plurality of separate imaging volumes 34. In an embodiment, the plurality of individual slices is defined automatically, for example by adjusting the imaging volume 34 of the magnetic resonance measurement as a function of the information about the jaw region 31 or based on the input of the user.

In a further step S8, an image of the diagnostically relevant area 32 of the jaw region 31 is reconstructed as a function of the captured image data of the jaw region of the patient.

The image of the diagnostically relevant area 32 of the jaw region 31 can be reconstructed as a function of the model of the jaw region 31 and/or as a function of the captured optical image data. The model of the jaw region 31 and/or the captured optical image data can be registered e.g. with the diagnostically relevant area 32. In this way, the position and/or the extent of the diagnostically relevant area 32 may be determined as a function of the model of the jaw region 31 and/or the captured optical image data by means of the computing unit 28. It is conceivable that image data of anatomical structures positioned outside of the diagnostically relevant area 32 is captured when carrying out the magnetic resonance measurement. Such anatomical structures can be identified when reconstructing the image of the diagnostically relevant area 32 of the jaw region 31 and be separated or faded out as a function of the model of the jaw region 31 and/or the optical image data. Furthermore, the image of the diagnostically relevant area 32 of the jaw region 31 can also be limited or restricted as a function of the model of the jaw region 31, the optical image data, and/or the localizer image data. In an embodiment, a portion of anatomical structures, which is situated outside of the diagnostically relevant area 32, is reduced or minimized to the reconstructed image.

In a further embodiment, reconstructing the image of the diagnostically relevant area 32 of the jaw region 31 comprises weighting image data of the plurality of antenna elements, with image data of areas outside of the diagnostically relevant area 32 of the jaw region 31 of the patient 15 being weighted to a lesser extent. A contrast and/or a transparency of image elements (pixels) can be adjusted during weighting in such a way that areas outside of the diagnostically relevant area 32 are faded out in the reconstructed image.

In a step S9, the image of the diagnostically relevant area 32 of the jaw region 31 of the patient 15 is provided.

In an embodiment, providing the image of the diagnostically relevant area 32 comprises at least storing the image of the diagnostically relevant area 32 on a memory unit 29 of the magnetic resonance apparatus 10, the cloud 30 and/or a medical information system. It is also conceivable that the image of the diagnostically relevant area 32 of the jaw region 31 is output to the user when provided by means of an output unit 24. The output unit 24 can be a monitor, a tablet, a smartphone, but also a printer.

Of course, the embodiments of the method and the magnetic resonance apparatus described herein should be understood as being exemplary. Individual embodiments can be expanded by features of other embodiments. Moreover, the order of the method steps of the method should be understood as being exemplary. The individual steps can also be carried out in a different order, partially, and/or completely overlap time-wise.

The various components described herein may be referred to as "units." As noted above, such components may be implemented via any suitable combination of hardware and/or software components as applicable and/or known to achieve the intended respective functionality. This may include mechanical and/or electrical components, FPGAs, processors, processing circuitry, or other suitable hardware components configured to execute instructions or computer programs that are stored on a suitable computer readable medium. Regardless of the particular implementation, such units, as applicable and relevant, may alternatively be referred to herein as "circuitry," "processors," or "processing circuitry."

What is claimed is:

1. A computer-implemented method for providing an image of a diagnostically relevant area of a jaw region of a patient via a magnetic resonance apparatus, comprising:
   receiving, via a computing unit, information associated with the jaw region of the patient, the received information comprising at least one reference to a position and/or an extent of the diagnostically relevant area of the jaw region;
   adjusting, via the computing unit a parameter of a magnetic resonance measurement as a function of the received information;
   executing, via the computing unit, the magnetic resonance measurement with the adjusted parameter;
   receiving, via the computing unit, image data of the jaw region of the patient;
   reconstructing, via the computing unit, an image of the diagnostically relevant area of the jaw region as a function of the received image data;
   generating, via the computing unit, the image of the diagnostically relevant area of the jaw region of the patient; and
   presenting, via a display, the image of the diagnostically relevant area of the jaw region of the patient.

2. A magnetic resonance apparatus, comprising:
   a patient-receiving area configured to receive a patient; and
   computing circuitry configured to:
      receive information associated with a jaw region of the patient, the received information comprising at least one reference to a position and/or an extent of a diagnostically relevant area of the jaw region of the patient;
      adjust a parameter of a magnetic resonance measurement as a function of the received information;
      execute the magnetic resonance measurement with the adjusted parameter;
      receive image data of the jaw region of the patient;
      reconstruct an image of the diagnostically relevant area of the jaw region as a function of the received image data;
      generate the image of the diagnostically relevant area of the jaw region of the patient; and
      cause a display to present the image of the diagnostically relevant area of the jaw region of the patient.

3. A non-transitory computer readable medium having instructions stored thereon that, when executed via one or more processors identified with a magnetic resonance apparatus, cause the magnetic resonance apparatus to:
   receive, via a computing unit, information associated with a jaw region of a patient, the received information comprising at least one reference to a position and/or an extent of a diagnostically relevant area of the jaw region of the patient;
   adjust, via the computing unit, a parameter of a magnetic resonance measurement as a function of the received information;
   execute, via the computing unit, the magnetic resonance measurement with the adjusted parameter;
   receive, via the computing unit, image data of the jaw region of the patient;
   reconstruct, via the computing unit, an image of the diagnostically relevant area of the jaw region as a function of the received image data;
   generate, via the computing unit, the image of the diagnostically relevant area of the jaw region of the patient; and
   present, via a display, the image of the diagnostically relevant area of the jaw region of the patient.

4. The computer-implemented method as claimed in claim 1, wherein the act of receiving the information associated with the jaw region of the patient comprises receiving one or more of:
   optical image data of a set of teeth of the patient,
   an X-ray image of the jaw region of the patient,
   a magnetic resonance image of the jaw region of the patient, and
   localizer image data of the jaw region of the patient.

5. The computer-implemented method as claimed in claim 1, wherein the act of receiving the information associated with the jaw region of the patient comprises:
   receiving optical image data associated with a set of teeth of the patient, and
   wherein at least one of the acts of adjusting the parameter of the magnetic resonance measurement and reconstructing the image of the diagnostically relevant area of the jaw region are performed as a function of the optical image data.

6. The computer-implemented method as claimed in claim 1, further comprising:
   adjusting a model of the jaw region of the patient as a function of the received information associated with the jaw region of the patient,
   wherein at least one of the acts of adjusting the parameter of the magnetic resonance measurement and reconstructing the image of the diagnostically relevant area of the jaw region is performed as a function of the model of the jaw region.

7. The computer-implemented method as claimed in claim 1, wherein the act of receiving the information associated with the jaw region of the patient further comprises:
   calculating a relative position of a first anatomical structure of the jaw region of the patient and a second anatomical structure of the jaw region of the patient, and
   wherein the act of adjusting the parameter of the magnetic resonance measurement is performed as a function of the relative position of the first anatomical structure of the jaw region of the patient and the second anatomical structure of the jaw region of the patient.

8. The computer-implemented method as claimed in claim 1, wherein:
   a plurality of individual slices is determined in the diagnostically relevant area of the jaw region as a function of the information about the jaw region of the patient,
   the act of adjusting the parameter of the magnetic resonance measurement is performed as a function of the plurality of individual slices, and
   executing the magnetic resonance measurement comprises receiving image data of the plurality of individual slices.

9. The computer-implemented method as claimed in claim 1, wherein the act of adjusting the parameter of the magnetic resonance measurement comprises one or more of:
   adjusting an imaging parameter of the magnetic resonance measurement,
   limiting an imaging volume of the magnetic resonance measurement to the diagnostically relevant area, and
   adjusting a phase encoding and/or a frequency encoding.

10. The computer-implemented method as claimed in claim 1, wherein the act of executing the magnetic resonance measurement comprises one or more of:
- selecting at least one antenna element from a plurality of antenna elements, the image data of the jaw region being received via the at least one selected antenna element;
- selectively exciting the diagnostically relevant area of the jaw region via an excitation pulse; and
- saturating nuclear spins in an area outside an imaging volume by emitting a saturation pulse as a function of the received information associated with the jaw region.

11. The computer-implemented method as claimed in claim 1, further comprising:
- generating, via a display, a representation of the jaw region of the patient as a function of the received information associated with the jaw region of the patient,
- wherein the representation of the jaw region has at least two regions, each respectively comprising a partial volume of the jaw region of the patient, at least one region of the at least two regions comprising at least part of the diagnostically relevant area;
- receiving a user input of the magnetic resonance apparatus, the user input comprising a selection of at least one region of the representation of the jaw region of the patient, and
- wherein at least one of the acts of adjusting the parameter of the magnetic resonance measurement and executing the magnetic resonance measurement are performed as a function of the user input.

12. The computer-implemented method as claimed in claim 1, wherein the act of adjusting the parameter of the magnetic resonance measurement comprises:
- determining a position of an antenna element as a function of at least one of the received information associated with the jaw region and a user input, and further comprising:
- positioning the antenna element at the jaw region of the patient as a function of the position,
- wherein the act of executing the magnetic resonance measurement comprises receiving image data of the jaw region of the patient via the positioned antenna element.

13. The computer-implemented method as claimed in claim 1, wherein:
- the act of receiving the image data of the jaw region is performed via a plurality of antenna elements,
- the act of reconstructing the image of the diagnostically relevant area of the jaw region comprises weighting image data of the plurality of antenna elements, and
- image data identified with areas outside of the diagnostically relevant area of the jaw region of the patient are weighted to a lesser extent than image data identified with areas inside of the diagnostically relevant area.

14. The computer-implemented method as claimed in claim 1, wherein:
- the act of receiving the image data of the jaw region comprises receiving image data of an anatomical structure outside of the jaw region of the patient,
- the act of reconstructing the image of the jaw region of the patient comprises identifying the anatomical structure in the image of the diagnostically relevant area of the jaw region of the patient, and
- the identified anatomical structure is faded out in the image of the diagnostically relevant area of the jaw region of the patient.

15. The computer-implemented method as claimed in claim 6, wherein the act of reconstructing the image of the diagnostically relevant area of the jaw region is performed as a function of the model of the jaw region, and
- wherein image data identified with areas outside of the diagnostically relevant area of the jaw region of the patient are faded out as a function of the model of the jaw region.

16. The computer-implemented method as claimed in claim 1, wherein the act of adjusting the parameter of the magnetic resonance measurement is performed as a function of a relative position of a first anatomical structure of the jaw region of the patient and a second anatomical structure of the jaw region of the patient.

17. The computer-implemented method as claimed in claim 1, wherein:
- the act of adjusting the parameter of the magnetic resonance measurement is performed as a function of a plurality of individual slices in a diagnostically relevant area of the jaw region, and
- executing the magnetic resonance measurement comprises receiving image data of the plurality of individual slices.

18. The computer-implemented method as claimed in claim 1, further comprising:
- positioning an antenna element at the jaw region of the patient,
- wherein the act of executing the magnetic resonance measurement comprises receiving image data of the jaw region of the patient via the positioned antenna element.

19. The computer-implemented method as claimed in claim 1, wherein:
- the act of reconstructing the image of the diagnostically relevant area of the jaw region comprises weighting image data of a plurality of antenna elements, and
- image data identified with areas outside of the diagnostically relevant area of the jaw region of the patient are weighted to a lesser extent than image data identified with areas inside of the diagnostically relevant area.

20. The computer-implemented method as claimed in claim 1, wherein the parameter comprises an image resolution, a contrast, a slice thickness, a dimension of an imaging volume, an imaging sequence, a succession of imaging sequences, a setting of the magnetic resonance measurement, and/or a progress of the magnetic resonance measurement.

* * * * *